March 9, 1937. P. A. IZZO Plant Pat. 236
ROSE
Filed Sept. 17, 1935
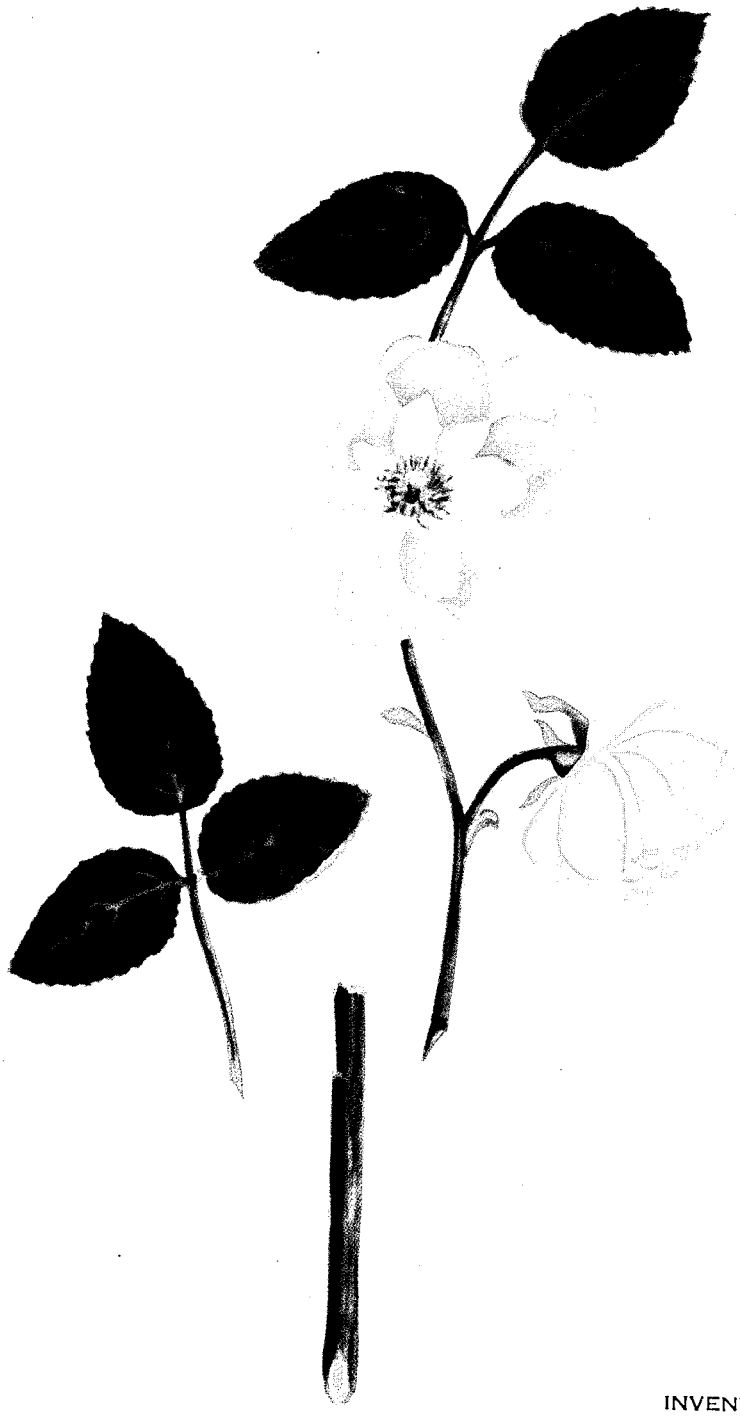
INVENTOR
PATSY A. IZZO
BY
Wiesen & Schrenk
ATTORNEYS Patented Mar. 9, 1937

Plant Pat. 236

UNITED STATES PATENT OFFICE

236

ROSE

Patsy A. Izzo, Glen Head, N. Y.

Application September 17, 1935, Serial No. 40,901

1 Claim. (Cl. 47—61)

The present invention relates to a new variety of rose of the ever-blooming hardy climbing type, the most novel characteristic of which is its being entirely thornless. This characteristic is present throughout all the stages of growth of the plant. A further novel characteristic of my new variety of rose is the vivid pink color of its petals.

The object of my invention is to provide a new and distinct variety of rose of the type described having desirable and pleasing characteristics not previously existing in any known variety of rose. More specifically my invention consists in the production of a new and distinct variety of climbing rose which is thornless throughout the plant, is characterized by the vivid pink color of its petals resembling the bush rose Editor McFarland, and is ever-blooming and hardy. The canes of my new variety of plant are vigorous in growth and upright in their development.

The accompanying illustrations show in full color my novel and distinct variety of plant, one flower being shown fully opened and one partly opened. The drawing further illustrates the characteristic features of the leaves and stem of the rose, only three leaflets being shown although the rose is characterized by five leaflets which are always serrate.

This new variety was originated by seeding, in 1931, and first asexually propagated by budding, in 1932. All of its characteristics have been thoroughly established through three asexual generations, over a period of three years.

The following is a detailed description of the characteristics and distinguishing features of the rose, but it must be understood that there may be some variation as between particular specimens of the new variety of plant:

*Stems.*—The canes of my new variety of rose are dark green with dark green foliage. New foliage developed during the growth of the plant tends to be reddish in color. The growth of the canes is vigorous and upright.

*Foliage.*—The leaves are medium size, dark green and disease resistant. The leaves are serrate along the edges, borne five to a branch on mature and immature canes, the size of a leaflet being approximately 2½'' long by 1½'' wide.

*Petalage.*—The flower of my novel variety of rose is characterized by a clear vivid pink color, unfading and fragrant, having about twenty petals to the flower. The color of my new variety of rose is a brighter pink than that of the climbing rose Mary Wallace, and both in bud and flower, a much clearer pink than Climbing Lady Ashtown. Such color may be classified, in accordance with color nomenclature as determined by the French Repertoire de Couleurs, as follows: inside of petals, Tyrian Rose, page 155; outside, Crimson Carmine, page 159; and, in accordance with Ridgway's Color Standards and Nomenclature, as follows: inside of petals, Clear Rose, Plate XII—71—V—RR, and the outside, Amarainth Pink, Plate XII—69—RV—R. When the flower is opened, it measures approximately 3'' across, the buds being long and pointed, borne on long stems, usually one bud to a stem but also in clusters of two or more on a single stem. The flower, as hereinabove described, has the desirable qualities rendering it most pleasing as a cut flower.

*Pollen.*—Yellow. The rose does not self-pollinate.

*Blooming.*—The rose starts to bloom in the latter part of May, bursts forth in a real splash of flowers, and when established throughout the spring is one mass of bloom. Blooming is continued throughout the summer but is not so profuse as at the beginning of its blooming period.

A more particular description of my novel variety of rose in accordance with the Gravereaux system of variety identification is as follows:

Parentage:

Unnamed seedlings.

Seeds were collected from many varieties of climbers in the field.

Classification:

Hardy climber.

*Flower*

Blooming habit:

Observations were made at Brookville and Glen Cove, New York.

Blooms profusely in spring; intermittent through the summer.

Bud:

*Size:*—Large.

*Form:*—Pointed.

*Opening:*—Bud opens well.

Unaffected by adverse conditions.

Bloom:

*Size:*—Large. Measuring about three inches when fully expanded.

*Borne:*—Singly on present season's growth and several together on the previous season's growth.

*Stems:*—Long. Normal.

*Petalage:*—Double; 20 under normal conditions.

*Color:*—Clear vivid pink resembling the bush rose Editor McFarland.

*Variegations:*—None.
*Discoloration:*—Unfading.
Petals:
*Texture:*—Soft. Unaffected by weather conditions.
*Form:*—Oval.
*Arrangement:*—Imbricated.
*Persistence:*—Drop off cleanly.
*Fragrance:*—Slight. Nature—"Old Rose perfume".
*Lasting quality:*—On the plant—good. As cut flower—good.
Genital organs:
*Stamens, anthers:*—Medium; many. Color—yellow. Arrangement—regular around styles.
*Stamens, filaments:*—Medium. Color—yellow.
*Pollen:*—Gold yellow.
*Styles:*—Bunched, even length. Medium. Heavy.
*Stigmas:*—Color—yellow.
*Ovaries:*—All enclosed in calyx.
Fruit:
Variety is sterile with its own pollen.

*Plant*

Form:
Climber.
Growth:
Vigorous, upright.
Foliage:
5 leaflets.
*Size:*—Medium.
*Quantity:*—Normal.
*Color:*—New foliage: reddish. Old foliage: dark green.
*Shape:*—Oval.
*Texture:*—Upper side — smooth. Ribs and veins: ordinary.
*Edge:*—Serrated.
*Serration:*—Single.
*Rachis:*—Color—green.
*Disease resistance:*—Resistant.
Wood:
*New wood:*—Color—reddish. Bark—smooth.
*Old wood:*—Color—green. Bark—smooth.
Thorns:
Thornless.

It is to be understood that the foregoing characteristics are typical but subject perhaps to slight variations which may arise by reason of change of environment.

I claim:

The rose herein shown and described characterized particularly by being entirely thornless, the vivid pink coloration of its flower, and its ever blooming and hardy climbing quality.

PATSY A. IZZO.